United States Patent
Chan et al.

[11] Patent Number: 5,852,397
[45] Date of Patent: Dec. 22, 1998

[54] ELECTRICAL DEVICES

[75] Inventors: Chi-Ming Chan, Kowloon; Michael Zhang, Talkoo Shing, both of Hong Kong; Daniel Chandler, Menlo Park, Calif.; Shou-Mean Fang, Yokohama, Japan; Dennis Siden, Portola Valley; Mark Thompson, San Carlos, both of Calif.

[73] Assignee: Raychem Corporation, Menlo Park, Calif.

[21] Appl. No.: 900,787

[22] Filed: Jul. 25, 1997

Related U.S. Application Data

[63] Continuation of Ser. No. 727,869, Oct. 8, 1996, abandoned, which is a continuation of Ser. No. 302,138, Sep. 7, 1994, abandoned, which is a continuation-in-part of Ser. No. 121,717, Sep. 15, 1993, abandoned, and Ser. No. 152,070, Nov. 12, 1993, abandoned, which is a continuation of Ser. No. 910,950, Jul. 9, 1992, abandoned.

[51] Int. Cl.⁶ .................................................. H01C 7/10
[52] U.S. Cl. .................................. 338/22 R; 338/22 SD; 338/312; 338/314
[58] Field of Search ......................... 338/22 R, 21, 338/22 SD, 220, 221, 312, 314

[56] References Cited

U.S. PATENT DOCUMENTS

| | | | |
|---|---|---|---|
| 3,221,145 | 11/1965 | Hager, Jr. ................................. | 219/549 |
| 3,351,882 | 11/1967 | Kohler et al. ............................ | 338/322 |
| 3,435,399 | 3/1969 | Gielisse et al. ........................ | 338/22 R |
| 3,497,859 | 2/1970 | Bang ....................................... | 338/309 |
| 3,648,364 | 3/1972 | Endo ....................................... | 29/620 |
| 3,775,725 | 11/1973 | Endo ....................................... | 338/262 |
| 3,835,434 | 9/1974 | Kahn ...................................... | 338/22 R |
| 4,237,441 | 12/1980 | van Konynenburg et al. ....... | 338/22 R |

(List continued on next page.)

FOREIGN PATENT DOCUMENTS

| | | |
|---|---|---|
| 0 223 404 | 5/1987 | European Pat. Off. . |
| 0 308 306 | 3/1989 | European Pat. Off. . |
| 0 398 811 | 11/1990 | European Pat. Off. . |
| 0 509 582 | 10/1992 | European Pat. Off. . |
| 31 22 612 | 12/1982 | Germany . |
| 87 16 103 | 3/1988 | Germany . |
| 38 39 868 | 6/1989 | Germany . |
| 39 10 861 | 11/1989 | Germany . |
| 49-28594 | 8/1974 | Japan . |
| 54-73260 | 6/1979 | Japan . |

(List continued on next page.)

OTHER PUBLICATIONS

"Protection of Batteries with PolySwitch® Devices", Raychem Corporation, Jan., 1987.
Search Report for International Application No. PCT/US93/06480, dated 7 Oct. 1994.
Search Report for International Application No. PCT/US94/10137, dated 23 Nov. 1993.
Search Report for International Application No. PCT/US95/05567, dated 26 Jun. 1995.

(List continued on next page.)

*Primary Examiner*—Tu Ba Hoang
*Attorney, Agent, or Firm*—Timothy H. P. Richardson; Herbert G. Burkard

[57] ABSTRACT

A circuit protection device which comprises first and second laminar electrodes; a laminar PTC conductive polymer resistive element sandwiched between the electrodes; a third laminar conductive member which is secured to the same face of the PTC element as the second electrode but is separated therefrom; and an electrical connector which connects the third conductive member and the first electrode. This permits connection to both electrodes from the same side of the device, so that the device can be connected flat on a printed circuit board, with the first electrode on top, without any need for leads. The connector is preferably a cross-conductor which passes through an aperture in the PTC element, because this makes it possible to carry out the steps for preparing the devices on an assembly which corresponds to a number of individual devices, with division of the assembly as the final step.

55 Claims, 5 Drawing Sheets

U.S. PATENT DOCUMENTS

| | | | |
|---|---|---|---|
| 4,238,812 | 12/1980 | Middleman et al. | 361/106 |
| 4,255,698 | 3/1981 | Simon | 320/35 |
| 4,272,471 | 6/1981 | Walker | 264/104 |
| 4,304,987 | 12/1981 | van Konynenburg | 219/553 |
| 4,315,237 | 2/1982 | Middleman et al. | 338/22 R |
| 4,317,027 | 2/1982 | Middleman et al. | 219/553 |
| 4,327,351 | 4/1982 | Walker | 338/22 R |
| 4,330,703 | 5/1982 | Horsma et al. | 219/553 |
| 4,352,083 | 9/1982 | Middleman et al. | 338/23 |
| 4,371,860 | 2/1983 | May et al. | 338/21 |
| 4,388,607 | 6/1983 | Toy et al. | 338/22 SD |
| 4,426,633 | 1/1984 | Taylor | 338/25 |
| 4,434,416 | 2/1984 | Schonberger | 338/203 |
| 4,445,026 | 4/1984 | Walker | 219/553 |
| 4,475,138 | 10/1984 | Middleman et al. | 361/58 |
| 4,486,737 | 12/1984 | Ott | 338/22 R |
| 4,486,738 | 12/1984 | Sadlo et al. | 338/320 |
| 4,514,620 | 4/1985 | Cheng et al. | 219/553 |
| 4,534,889 | 8/1985 | van Konynenburg et al. | 252/511 |
| 4,545,926 | 10/1985 | Fouts et al. | 252/511 |
| 4,560,498 | 12/1985 | Horsma et al. | 252/511 |
| 4,591,700 | 5/1986 | Sopory | 219/505 |
| 4,689,475 | 8/1987 | Kleiner et al. | 219/553 |
| 4,706,060 | 11/1987 | May | 338/20 |
| 4,724,417 | 2/1988 | Au et al. | 338/22 R |
| 4,757,298 | 7/1988 | Nishikawa et al. | 338/308 |
| 4,774,024 | 9/1988 | Deep et al. | 252/511 |
| 4,777,718 | 10/1988 | Henderson et al. | 338/312 X |
| 4,780,598 | 10/1988 | Fahey et al. | 219/511 |
| 4,786,888 | 11/1988 | Yoneda et al. | 338/22 R |
| 4,788,523 | 11/1988 | Robbins | 338/309 |
| 4,800,253 | 1/1989 | Kleiner et al. | 219/553 |
| 4,801,784 | 1/1989 | Jensen et al. | 338/22 R |
| 4,845,838 | 7/1989 | Jacobs et al. | 29/671 |
| 4,861,966 | 8/1989 | Matthiesen et al. | 219/205 |
| 4,876,439 | 10/1989 | Nagahori | 338/22 R |
| 4,882,466 | 11/1989 | Friel | 219/219 |
| 4,907,340 | 3/1990 | Fang et al. | 29/610.1 |
| 4,924,074 | 5/1990 | Fang et al. | 219/548 |
| 4,924,204 | 5/1990 | Uchida | 338/22 R |
| 4,924,205 | 5/1990 | Caporali et al. | 338/227 |
| 4,935,156 | 6/1990 | van Konynenburg et al. | 219/553 |
| 4,977,309 | 12/1990 | Uchida | 219/541 |
| 4,992,771 | 2/1991 | Caporali et al. | 338/22 R |
| 4,993,142 | 2/1991 | Burke et al. | 29/621 |
| 5,049,850 | 9/1991 | Evans et al. | 338/22 R |
| 5,212,466 | 5/1993 | Yamada et al. | 338/22 R |
| 5,216,404 | 6/1993 | Nagai et al. | 338/22 SD |
| 5,247,277 | 9/1993 | Fang et al. | 338/22 R |
| 5,280,263 | 1/1994 | Sugaya | 338/22 R |
| 5,303,115 | 4/1994 | Nayar et al. | 361/106 |
| 5,347,258 | 9/1994 | Howard et al. | 338/333 |
| 5,351,390 | 10/1994 | Yamada et al. | 29/612 |
| 5,451,921 | 9/1995 | Crawford et al. | 338/220 |

FOREIGN PATENT DOCUMENTS

| | | |
|---|---|---|
| 56-150802 | 11/1981 | Japan . |
| 63-216301 | 9/1988 | Japan . |
| 63-244702 | 10/1988 | Japan . |
| 1415454 | 11/1975 | United Kingdom . |
| WO 84/01259 | 3/1984 | WIPO . |
| WO 94/01876 | 1/1994 | WIPO . |
| WO 95/08176 | 3/1995 | WIPO . |
| WO 95/31816 | 11/1995 | WIPO . |

OTHER PUBLICATIONS

Search Report for International Application No. PCT/US95/07420, dated 4 Sep. 1995.

"PolySwitch PTC Devices, Standard Product List", Raychem Corporation, May 1992.

"PolySwitch SMD Surface Mount devices PTC overcurrent protection" trade brochure, Raychem Corporation, Nov. 1992.

"PolySwitch SMD Installation Guidelines" trade brochure, Raychem Corporation, Nov. 1992.

*Printed Circuit Handbook,* (Coombs, 1996) pp. 24.1–24.17.

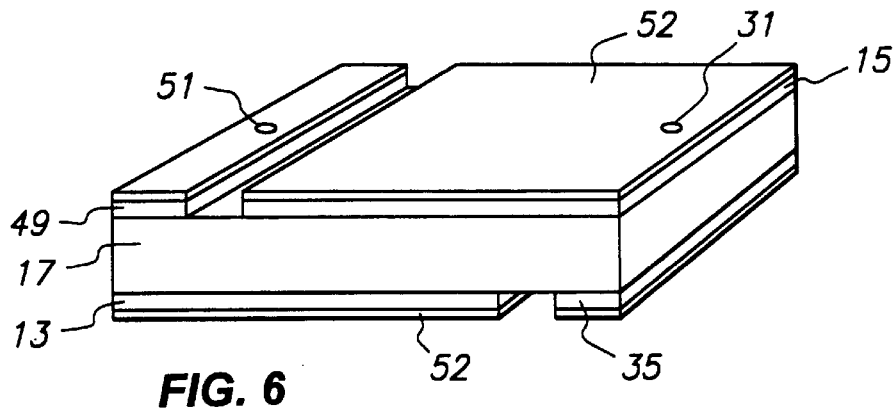
FIG. 5
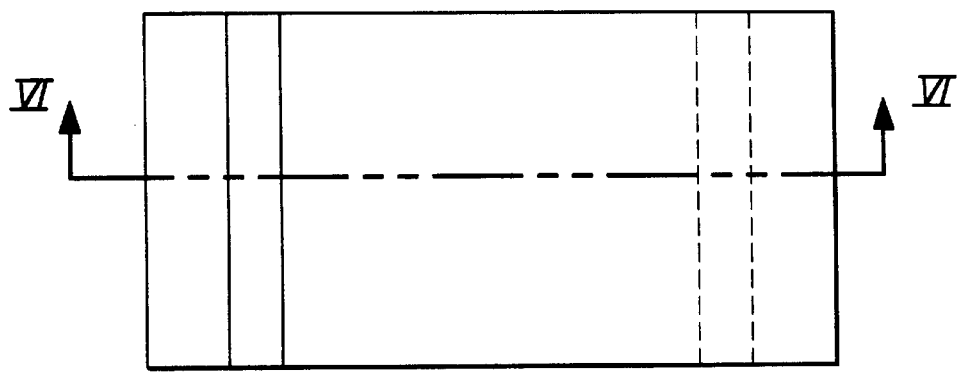
FIG. 6
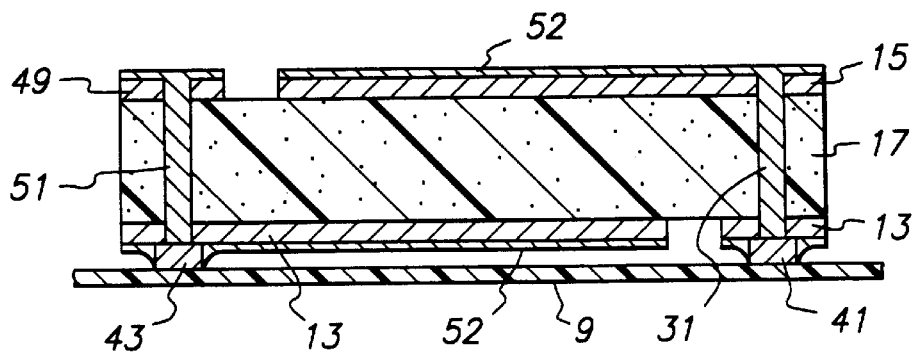
FIG. 7
FIG. 8

ELECTRICAL DEVICES

CROSS REFERENCE TO RELATED APPLICATIONS

This application is a continuation of U.S. patent application Ser. No. 08/727,869 filed Oct. 8, 1996, now abandoned, which is a continuation of U.S. patent application Ser. No. 08/302,138 filed Sep. 7, 1994, now abandoned, which is a continuation-in-part of (1) commonly assigned U.S. patent application Ser. No. 08/152,070, filed Nov. 12, 1993, by Graves, Zhang, Chandler, Chan and Fang, now abandoned, which is a file wrapper continuation of U.S. patent application Ser. No. 07/910,950, filed Jul. 9, 1992, now abandoned, and (2) commonly assigned U.S. patent application Ser. No. 08/121,717, filed Sep. 15, 1993, by Fang, Siden, Thompson and Zhang, now abandoned.

This application is also related to copending International Application No. PCT/US93/06480, filed Jul. 8, 1993, by Raychem Corporation, now published as WO 94/01876, which claims priority from U.S. patent application Ser. No. 07/910,950; to copending, commonly assigned U.S. patent application Ser. No. 08/242,916, filed May 16, 1994, by Zhang and Fang, now abandoned in favor of continuation application Ser. No. 08/710,925; and to copending, commonly assigned U.S. patent application Ser. No. 08/257,586, filed Jun. 9, 1994, by Zhang, Thompson, Toth and Beadling, now abandoned in favor of continuation application Ser. No. 08/808,135.

BACKGROUND OF THE INVENTION

1. Field of the Invention

This invention relates to electrical devices.

2. Introduction to the Invention

Many electrical devices comprise two laminar electrodes and, sandwiched between them, an electrical element which may be a conductor, e.g. a resistive element, as for example in a resistor or a varistor, or a non-conductor, as for example in a capacitor. Particularly useful devices of this type are circuit protection devices which comprise a laminate of two laminar electrodes and, sandwiched between the electrodes, a laminar resistive element which exhibits PTC behavior. The resistive element may be composed of conductive polymer (this term being used to denote a composition comprising a polymer and, dispersed, or otherwise distributed, therein, a particulate conductive filler) or a ceramic, e.g. a doped barium titanate. When a conductive polymer is used, such devices are generally prepared by stamping (or otherwise cutting) a plurality of the devices out of a laminate of a sheet of the conductive polymer between two metal foils. When a ceramic is used, such devices are usually prepared by applying liquid electrode material to the major surfaces of a preformed laminar resistive element, and solidifying the liquid electrode material.

The products of such processes can sometimes be used without the addition of electrical leads, for example by installation between two spring-loaded terminals. In most cases, however, an electrical lead must be secured to each of the laminar electrodes, so that the device can be connected to other components of a circuit, e.g. mounted on a circuit board. The addition of leads is an additional expense and usually involves heating (e.g. during soldering or welding) which can cause damage, particularly to conductive polymer elements. The latter problem is particularly severe when a conductive polymer is heated a second time when the leads are connected to other circuit elements, in particular when the leads are connected to a printed circuit board by a soldering process. A further problem which can arise when such devices are to be mounted on a printed circuit board is that they protrude further from the board than is desirable.

SUMMARY OF THE INVENTION

We have carried out development work on circuit protection devices which comprise two laminar electrodes and, sandwiched between them, a laminar PTC resistive element comprising a PTC conductive polymer; and we have realized that when such a device is to be connected to electrical conductors on an insulating substrate, parallel to the substrate, then by appropriate modification of the device, the connection can be made without the need for separate electrical leads.

In a first aspect, this invention provides a circuit protection device which comprises (1) a first laminar electrode;
(2) a second laminar electrode;
(3) a laminar PTC resistive element which (i) exhibits PTC behavior, (ii) comprises a laminar element composed of a PTC conductive polymer, (iii) has a first face to which the first electrode is secured and an opposite second face to which the second electrode is secured, and (iv) defines an aperture which runs between the first and second faces;
(4) a third laminar conductive member which (i) is secured to the second face of the PTC resistive element in the area of the aperture, and (ii) is spaced apart from the second electrode; and
(5) a transverse conductive member which
   (a) lies within the aperture defined by the PTC resistive element,
   (b) runs between the first and second faces of the PTC element,
   (c) is secured to the PTC element, and
   (d) is physically and electrically connected to the first laminar electrode and to the third laminar conductive member, but is not connected to the second laminar electrode.

The third laminar conductive member provides a conductive pad through which connection can be made to the first electrode, via the transverse conductive member, which is often referred to herein as a "cross-conductor". This third member is preferably a residual member formed by removing part of a laminar conductive member from an assembly comprising two laminar conductive members and a PTC element between them; the other part of the conductive member provides the second electrode.

To mount such a device flat on top of a printed circuit board (or other insulating substrate having conductors thereon), the device is placed on the substrate with the first electrode on top. The second electrode is connected directly to one conductor on the board, and the third conductive member is connected to another conductor on the board.

A preferred embodiment of the first aspect of the invention is a device which can be placed on the board with either electrode on top, the device preferably being symmetrical, so that the connections to the device and the subsequent operation of the device can be the same. Such a device comprises (1) a first laminar electrode;
(2) a second laminar electrode;
(3) a laminar PTC resistive element which (i) exhibits PTC behavior, (ii) comprises a laminar element composed of a PTC conductive polymer, (iii) has a first face to which the first electrode is secured and an opposite second face to which the second electrode is secured, and (iv) defines first and second apertures which runs between the first and second faces;

(4) a third laminar conductive member which (i) is secured to the second face of the PTC resistive element in the area of the first aperture, and (ii) is spaced apart from the second electrode;

(5) a fourth laminar conductive member which (i) is secured to the first face of the PTC resistive element in the area of the second aperture, and (ii) is spaced apart from the first electrode;

(6) a first transverse conductive member which
   (a) lies within the first aperture defined by the PTC resistive element,
   (b) runs between the first and second faces of the PTC element,
   (c) is secured to the PTC element, and
   (d) is physically and electrically connected to the first laminar electrode and to the third laminar conductive member, but is not connected to the second laminar electrode; and (7) a second transverse conductive member which
   (a) lies within the second aperture defined by the PTC resistive element,
   (b) runs between the first and second faces of the PTC element,
   (c) is secured to the PTC element, and
   (d) is physically and electrically connected to the second laminar electrode and to the fourth laminar conductive member, but is not connected to the first laminar electrode.

The novel devices of the invention can be made by securing electrodes of appropriate shapes to resistive elements of the desired final shape; or by securing electrode precursors of appropriate shapes to resistive elements which are larger than the desired final shape, and then dividing the assembly into a plurality of devices of the desired final shape or shapes; or by preparing a plurality of devices of the desired final shape or shapes by division of a simple laminate of constant cross-section and, if desired or necessary, and before or after the division, removing unwanted portions of one or both of the electrodes. Such removal can be effected for example by milling or by etching. Preferably such removal of unwanted portions of the electrodes removes little or none of the PTC resistive element, which provides desirable physical strength to the connection leg. The residual portion is not electrically connected to the main portion, but provides valuable physical properties, including strength and resistance to deformation when connection to the first electrode is made by a spring clip or other elastically deformed terminal. A preferred process for preparing devices of the invention is described in copending, commonly assigned U.S. patent application Ser. No. 08/257,586, now abandoned in favor of continuation application Ser. No. 08/808,135.

The devices of the first aspect of the invention are preferably made by processes in which various operative steps are carried out on an assembly which corresponds to a plurality of devices in both the longitudinal and the lateral dimension, and which, as the final step of the process, is divided into a plurality of devices. The ability to prepare devices in this way becomes increasingly important as the size(and, therefore, resistance) of the device decreases and this invention is especially valuable for preparing devices which are to be mounted on circuit boards and in other situations in which the smaller the size and resistance of the device, the better. For example, such a process can be used to make circuit protection devices having a surface area of about 0.02 inch$^2$ (13 mm$^2$) or even less.

A second aspect of the invention is an assembly which can be divided into a plurality of devices according to the first aspect of the invention, and which comprises (1) a plurality of first laminar conductive members in the form of parallel strips;

(2) a plurality of second laminar conductive members in the form of strips which are parallel to each other and to the first laminar conductive members, but which are staggered in relation to the first conductive members;

(3) a laminar PTC resistive element which (i) exhibits PTC behavior, (ii) comprises a laminar element composed of a PTC conductive polymer, (iii) has a first face to which the first conductive members are secured and an opposite second face to which the second conductive members are secured, and (iv) defines a plurality of apertures which run between the first and second faces; and (4) a plurality of transverse conductive members which are arranged in a plurality of straight lines parallel to the first and second laminar conductive members, and each of which
   (a) lies within an aperture defined by the PTC resistive element,
   (b) runs between the first and second faces of the PTC element,
   (c) is secured to the PTC element, and
   (d) is physically and electrically connected to one of the first laminar conductive members and to one of the second laminar conductive members.

A third aspect of the invention is a method of making a device according to the first aspect of the invention which comprises dividing an assembly according to the second aspect of the invention along lines which are parallel to the conductive members and along lines which are at right angles to the conductive members.

The various steps of the method are preferably carried out at a temperature substantially below the melting point of the PTC element, in order to minimize changes in its electrical properties.

Although it is preferred to use a cross conductor to connect the electrode(s) and the third (and fourth) conductive members, many benefits can be realized through the use of any type of electrical connector. Thus, a fourth aspect of this invention is a circuit protection device which comprises (1) a first laminar electrode;

(2) a second laminar electrode;

(3) a laminar resistive element which (i) exhibits PTC behavior, (ii) comprises a laminar element composed of a PTC conductive polymer, and (iii) has a first face to which the first electrode is secured and an opposite second face to which the second electrode is secured;

(4) a residual laminar conductive member which (i) is secured to the second face of the laminar resistive element and (ii) is spaced apart from the second electrode; and (5) an electrical connector which contacts the first electrode and the residual conductive member;

the device comprising (A) a main portion which comprises
   (i) a main part of the first electrode,
   (ii) a main part of the second electrode, and
   (iii) a main part of the resistive element; and (B) a connection leg which extends away from the main portion, and which comprises
  (a) a distal portion which
    (i) is spaced away from the main portion of the device, and
    (ii) comprises the residual laminar conductive member, a distal part of the first electrode, a distal part of the resistive element, and the electrical connector, the electrical connector contacting the distal part of the first electrode and extending beyond the second face of the distal part of the laminar resistive element to contact the residual laminar conductive member; and
  (b) a bridge portion which
    (i) lies between the distal portion and the main portion of the device,
    (ii) extends across the width of the connection leg,
    (iii) comprises a bridge part of the first electrode and a bridge part of the resistive element, and
    (iv) does not include any part of the second electrode;
  the main, bridge and distal parts of the first electrode being integral with each other; the main, bridge and distal parts of the resistive element being integral with each other; and the residual conductive member being such that, in the absence of the bridge portion, it would be integral with the second electrode;
whereby the device can be placed flat on a planar insulating substrate having first and second appropriately spaced-apart metal conductors on the surface thereof, with the electrical connector adjacent the first metal conductor, and the second electrode adjacent the second metal conductor; and electrical connection can be made (a) between the first metal conductor and the first electrode, through the electrical connector, and (b) between the second conductor and the second electrode. The electrical connector can be electrically connected to the first electrode before it is electrically connected to the conductor on the substrate, or both connections can be made simultaneously.

A preferred embodiment of the fourth aspect of the invention is a device which can be connected to a board with either electrode on top, and which comprises (1) a first laminar electrode;
(2) a second laminar electrode;
(3) a laminar resistive element which (i) exhibits PTC behavior, (ii) comprises a laminar element composed of a PTC conductive polymer, and (iii) has a first face to which the first electrode is secured and an opposite second face to which the second electrode is secured;
(4) a first residual laminar conductive member which (i) is secured to the second face of the laminar resistive element and (ii) is spaced apart from the second electrode;
(5) a second residual laminar conductive member which (i) is secured to the first face of the laminar resistive element and (ii) is spaced apart from the first electrode;
(6) a first electrical connector which contacts the first electrode and the first residual conductive member; and
(7) a second electrical connector which contacts the second electrode and the second residual conductive member;
the device comprising
(A) a main portion which comprises
  (i) a main part of the first electrode,
  (ii) a main part of the second electrode, and
  (iii) a main part of the resistive element;

(B) a first connection leg which extends away from the main portion, and which comprises
  (a) a first distal portion which
    (i) is spaced away from the main portion of the device, and
    (ii) comprises the first residual conductive member; a distal part of the first electrode, a first distal part of the resistive element, and the first electrical connector, the first electrical connector contacting the distal part of the first electrode and extending beyond the second face of the first distal part of the laminar resistive element into contact with the first residual conductive member; and
  (b) a first bridge portion which
    (i) lies between the first distal portion and the main portion of the device,
    (ii) extends across the width of the first connection leg,
    (iii) comprises a bridge part of the first electrode and a first bridge part of the resistive element, and
    (iv) does not include any part of the second electrode;
  the main, bridge and distal parts of the first electrode being integral with each other; the main, first bridge and first distal parts of the resistive element being integral with each other; and the first residual conductive member being such that, in the absence of the bridge portion, it would be integral with the second electrode; and
(C) a second connection leg which extends away from the main portion, and which comprises
  (a) a second distal portion which
    (i) is spaced away from the main portion of the device, and
    (ii) comprises the second residual conductive member, a distal part of the second electrode, a second distal part of the resistive element, and the second electrical connector, the second electrical connector contacting the distal part of the second electrode and extending beyond the second face of the second distal part of the laminar resistive element into contact with the second residual conductive member; and
  (b) a second bridge portion which
    (i) lies between the second distal portion and the main portion of the device,
    (ii) extends across the width of the second connection leg,
    (iii) comprises a bridge part of the second electrode and a second bridge part of the resistive element, and
    (iv) does not include any part of the first electrode;
  the main, bridge and distal parts of the second electrode being integral with each other; the main, second bridge and second distal parts of the resistive element being integral with each other; and the second residual conductive member being such that in the absence of the bridge portion it would be integral with the first electrode;
whereby the device can be placed either way up flat on a planar insulating substrate having first and second appropriately spaced-apart metal conductors on the surface thereof, with the first or the second electrical connector adjacent the first metal conductor, and the second or the first electrode adjacent the second metal conductor; and electrical connection can be made (a) between the first metal conductor and the first electrode, through the first electrical connector, or between the first metal conductor and the second electrode, through the second electrical connector, and (b) between the second conductor and the second electrode, or between the second conductor and the first electrode.

BRIEF DESCRIPTION OF THE DRAWINGS

The invention is illustrated in the accompanying drawings, in which

FIGS. 4 and 5 are cross sectional views of devices of the first aspect of the invention;

FIG. 6 is a perspective view of a device of the first aspect of the invention;

FIGS. 7 and 8 are plan and cross sectional views of the device of FIG. 6 mounted on a printed circuit board parallel to the board;

DETAILED DESCRIPTION OF THE INVENTION

Figure 1:
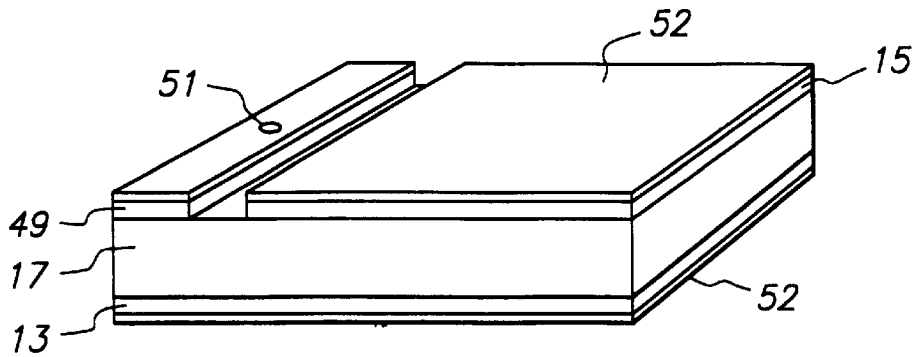
FIGS. 1, 2 and 3 are perspective, plan and cross sectional views of a device of the first aspect of the invention.

All embodiments and aspects of the invention set out below are to be regarded as part of Applicants' invention, even where the following detailed description is broader than the summary of the invention set out above. Conversely, the following detailed description should not be regarded as in any way limiting the generality of the summary of the invention set out above.

As described and claimed below, and as illustrated in the accompanying drawings, the present invention can make use of a number of particular features. Where such feature is disclosed in a particular context or as part of a particular combination, it can also be used in other contexts and in other combinations, including for example other combinations of two or more such features.

PTC Compositions

The PTC compositions used in the present invention are conductive polymers which comprise a crystalline polymer component and, dispersed in the polymer component, a particulate filler component which comprises a conductive filler, e.g. carbon black or a metal. The filler component may also contain a non-conductive filler, which changes not only the electrical properties of the conductive polymer but also its physical properties. The composition can also contain one or more other components, e.g. an antioxidant, crosslinking agent, coupling agent or elastomer. The PTC composition preferably has a resistivity at 23° C. of less than 50 ohm-cm, particularly less than 10 ohm-cm, especially less than 5 ohm-cm. Suitable conductive polymers for use in this invention are disclosed for example in U.S. Pat. No. 4,237,441 (van Konynenburg et al), U.S. Pat. No. 4,304,987 (van Konynenburg), U.S. Pat. No. 4,388,607 (Toy et al), U.S. Pat. No. 4,514,620 (Cheng et al), U.S. Pat. No. 4,534,889 (van Konynenburg et al), U.S. Pat. No. 4,545,926 (Fouts et al), U.S. Pat. No. 4,560,498 (Horsma et al), U.S. Pat. No. 4,591,700 (Sopory), U.S. Pat. No. 4,724,417 (Au et al), U.S. Pat. No. 4,774,024 (Deep et al), U.S. Pat. No. 4,935,156 (van Konynenburg), and U.S. Pat. No. 5,049,850 (Evans et al). The disclosure of each of those patents is incorporated herein by reference.

The PTC resistive element is a laminar element, and can be composed of one or more conductive polymer members, at least one of which is composed of a PTC material. When there is more than one conductive polymer member, the current preferably flows sequentially through the different compositions, as for example when each composition is in the form of a layer which extends across the whole device. When there is a single PTC composition, and the desired thickness of the PTC element is greater than that which can conveniently be prepared in a single step, a PTC element of the desired thickness can conveniently be prepared by joining together, e.g. laminating by means of heat and pressure, two or more layers, e.g. melt-extruded layers, of the PTC composition. When there is more than one PTC composition, the PTC element will usually be prepared by joining together. e.g. laminating by means of heat and pressure, elements of the different compositions. For example, a PTC element can comprise two laminar elements composed of a first PTC composition and, sandwiched between them, a laminar element composed of a second PTC composition having a higher resistivity than the first.

When a PTC device is tripped, most of the voltage dropped over the device is normally dropped over a relatively small part of the device which is referred to as the hot line, hot plane or hot zone. In the devices of the invention, the PTC element can have one or more features which help the hot line to form at a desired location, usually spaced apart from both electrodes. Suitable features of this kind for use in the present invention are disclosed for example in U.S. Pat. Nos. 4,317,027 and 4,352,083 (Middleman et al), U.S. Pat. Nos. 4,907,340 and 4,924,072 (Fang et al), the disclosures of which are incorporated herein by reference.

Laminar Electrodes

Particularly useful devices of the invention comprise two metal foil electrodes, and a PTC conductive polymer element sandwiched between them, especially such devices which have low resistance at 23° C., generally less than 50 ohm, preferably less than 15 ohm, more preferably less than 10 ohm, particularly less than 5 ohm, especially less than 3 ohm, with yet lower resistance being possible, e.g. less than 1 ohm, even less than 0.5 ohm. Particularly suitable foil electrodes are microrough metal foil electrodes, including in particular electrodeposited nickel foils and nickel-plated electrodeposited copper foil electrodes, in particular as disclosed in U.S. Pat. No. 4,689,475 (Matthieson) and U.S. Pat. No. 4,800,253 (Kleiner et al), the disclosure of each of which is incorporated herein by reference. A variety of laminar devices which can be modified in accordance with the present invention are disclosed in U.S. Pat. No. 4,238,812 (Middleman et al), U.S. Pat. No. 4,255,798 (Simon), U.S. Pat. No. 4,272,471 (Walker), U.S. Pat. No. 4,315,237 (Middleman et al), U.S. Pat. No. 4,317,027 (Middleman et al), U.S. Pat. No. 4,330,703 (Horsma et al), U.S. Pat. No. 4,426,633 (Taylor), U.S. Pat. No. 4,475,138 (Middleman et al), U.S. Pat. No. 4,724,417 (Au et al), U.S. Pat. No. 4,780,598 (Fahey et al, U.S. Pat. No. 4,845,838 (Jacobs et al), U.S. Pat. No. 4,907,340 (Fang et al), and U.S. Pat. No.

4,924,074 (Fang et al), the disclosure of each of which is incorporated herein by reference. The electrodes can be modified so as to produce desired thermal effects.

The electrodes are preferably secured directly to the PTC resistive element.

Apertures and Cross-Conductors

The term "aperture" is used herein to denote an opening which, when viewed at right angles to the plane of the device, (a) has a closed cross section, e.g. a circle, an oval, or a generally rectangular shape, or (b) has a reentrant cross section, the term "reentrant cross section" being used to denote an open cross section which (i) has a depth at least 0.15 times, preferably at least 0.5 times, particularly at least 1.2 times, the maximum width of the cross section, e.g. a quarter circle or a half circle or an open-ended slot, and/or (ii) has at least one part where the opposite edges of the cross section are parallel to each other.

In assemblies of the invention which can be divided into a plurality of electrical devices, the apertures will normally be of closed cross section, but if one or more of the lines of division passes through an aperture of closed cross section, then the apertures in the resulting devices will then have open cross sections. It is important that any such open cross section is a reentrant cross section as defined above, in order to ensure that the cross-conductor is not damaged or dislodged during installation or use of the device.

The aperture can be a circular hole, and for many purposes this is satisfactory in both individual devices and assemblies of devices. However, if the assembly includes apertures which are traversed by at least one line of division, elongate apertures may be preferred because they require less accuracy in the lines of division.

When the aperture is not traversed by a line of division, it can be as small as is convenient for a cross-conductor having the necessary current-carrying capacity. For circuit protection devices, holes of diameter 0.1 to 5 mm, preferably 0.15 to 1.0 mm, e.g. 0.2 to 0.5 mm, are generally satisfactory. Generally a single cross-conductor is all that is needed to make an electrical connection to the first electrode from the opposite side of the device. However, two or more cross-conductors can be used to make the same connection. The number and size of the cross-conductors, and, therefore, their thermal capacity, can have an appreciable influence on the rate at which a circuit protection device will trip.

The aperture can be formed before the cross-conductor is put in place, or the formation of the aperture and the placing of the cross-conductor can be carried out simultaneously. A preferred procedure is to form the aperture, e.g. by drilling, slicing or any other appropriate technique, and then to plate or otherwise coat or fill the interior surface of the aperture. The plating can be effected by electroless plating, or electrolytic plating, or by a combination of both. The plating can be a single layer or multiple layers, and can be composed of a single metal or a mixture of metals, in particular a solder. The plating will often also be formed on other exposed conductive surfaces of the assembly. If such plating is not desired, then the other exposed conductive surfaces must be masked or otherwise desensitized. Generally, however, the plating is carried out at a stage of the process at which such additional plating will not produce an adverse effect. The invention includes the possibility that the plating will produce not only the cross-conductor but also at least part of the laminar conductive members in the device.

The plating techniques which are used for making conductive vias through insulating circuit boards can be used in the present invention. However, in this invention the plating serves merely to convey current across the device, whereas a plated via must make good electrical contact with another component. Consequently, the plating quality required in this invention may be less than that required for a via.

Another technique for providing the cross-conductors is to place a moldable or liquid conductive composition in preformed apertures, and if desired or necessary to treat the composition, while it is in the apertures, so as to produce cross-conductors of desired properties. The composition can be supplied selectively to the apertures, e.g. by means of a screen, or to the whole assembly, if desired after pretreating at least some of the assembly so that the composition does not stick to it. For example, a molten conductive composition, e.g. solder, could be used in this way, if desired using wave soldering techniques.

The cross-conductor can also be provided by a preformed member, e.g. a metal rod or tube, for example a rivet. When such a preformed member is used, it can create the aperture as it is put in place in the device.

The cross-conductor can partially or completely fill the aperture. When the aperture is partially filled, it can be further filled (including completely filled) during the process in which the device is connected to other electrical components, particularly by a soldering process. This can be encouraged by providing additional solder in and around the aperture, especially by including a plating of solder in and around the aperture. Normally at least a part of the cross-conductor will be put in place before the device is connected to other electrical components.

However, the invention includes the possibility that the cross-conductor is formed during such a connection process, as for example by the capillary action of solder during a soldering process.

Connectors which are not Cross-Conductors

The electrical connection(s) between the electrode(s) and the residual member(s) on the opposite face of the PTC resistive element is preferably through a cross-conductor as described in detail above. However, it can be of any kind, for example a connector which will remain in place even if it is not bonded to the other parts of the device, for example a U-shaped member which extends around the end of the first leg portion and the first electrode and, if present, the second residual conductive member. The connector can be resilient so that it clamps to the remainder of the device.

Third Laminar Conductive Members

The third laminar conductive member which, with the cross conductor or other connector, provides an electrical path to the first electrode is preferably a residual member formed by removing part of a laminar conductive member, the remainder of the laminar conductive member then being the second electrode. The shape of the third member, and the shape of the gap between the third member and the second electrode, can be varied to suit the desired characteristics of the device and for ease of manufacture. Thus the third member is conveniently a small rectangle at one end of a rectangular device, separated from the second electrode by a rectangular gap, as shown for example in FIGS. 1–3; but other arrangements are possible. For example the third member can be an island separated from the second electrode by a gap of closed cross section. If two or more devices in parallel are needed, there can be two or more second electrodes on the second face of the PTC element, with a single first electrode which is on the first face of the PTC element and to which connection is made via the cross-conductor or other connector. When two or more devices in series are required, the third member of one device can be connected to the second electrode of the adjacent device; the devices can be joined together by non-current-carrying sections of the PTC conductive polymer element, or otherwise.

Devices

In the simplest devices, there is a single first electrode, a single cross-conductor or other connector, a single third member, and a single second electrode. Such devices are illustrated in FIGS. 1–5. A disadvantage of such a device is that it must be placed on the circuit board the right way up. This disadvantage can be overcome (at the expense of additional material and processing costs) by making a device which also has a fourth laminar conductive member and a second cross-conductor or other connector. Such devices are illustrated in FIGS. 6 to 11, and 14 and 15.

Particularly preferred circuit protection devices of the invention have a resistance at 23° C. of less than 15 ohm, preferably less than 10 ohm, particularly less than 5 ohm, especially less than 1 ohm, and comprise (1) a laminar PTC resistive element which
   (a) is composed of a conductive polymer which has a resistivity at 25° C. of less than 50 ohm-cm, preferably less than 10 ohm-cm, particularly less than 5 ohm-cm, and which exhibits PTC behavior, and
   (b) has a first face and second face;
(2) a first metal foil electrode which contacts the first face of the PTC element,
(3) a second metal foil electrode which contacts the second face of the PTC element; and
(4) an additional metal foil conductive member which contacts the second face of the PTC element and is spaced apart from the second electrode;

the PTC element, the first electrode and the additional conductive member defining an aperture which runs between the first electrode and the additional conductive member, through the PTC element, and (5) a transverse conductive member which
   (a) is composed of metal,
   (b) lies within the aperture, and
   (c) is physically and electrically connected to the first electrode and the additional conductive member.

The devices of the invention can be of any appropriate size. However, it is an important advantage of the use of cross conductors in accordance with the first aspect of the invention that very small devices can be easily prepared. Preferred devices have a maximum dimension of at most 12 mm, preferably at most 7 mm, and/or a surface area of at most 30 mm$^2$, preferably at most 20 mm$^2$, especially at most 15 mm$^2$.

Processes

The devices of the invention containing cross-conductors can be prepared in any way. However, the preferred methods of the invention make it possible to prepare devices very economically by carrying out all or most of the process steps on a large laminate, and then dividing the laminate into a plurality of individual devices, or into relatively small groups of devices which are connected together physically and which may be connected to each other electrically, in series or in parallel or both. The division of the laminate can be carried out along lines which pass through one or both or neither of the laminar conductive members or through none, some or all of the cross-conductors. The process steps prior to division can in general be carried out in any convenient sequence. Preferred processes for making the devices are disclosed in U.S. patent application Ser. No. 08/242,916, now abandoned in favor of continuation application Ser. No. 08/710,925, and Ser. No. 08/257,586, now abandoned in favor of continuation application Ser. No. 08/838,135.

Drawings

Figure 2:
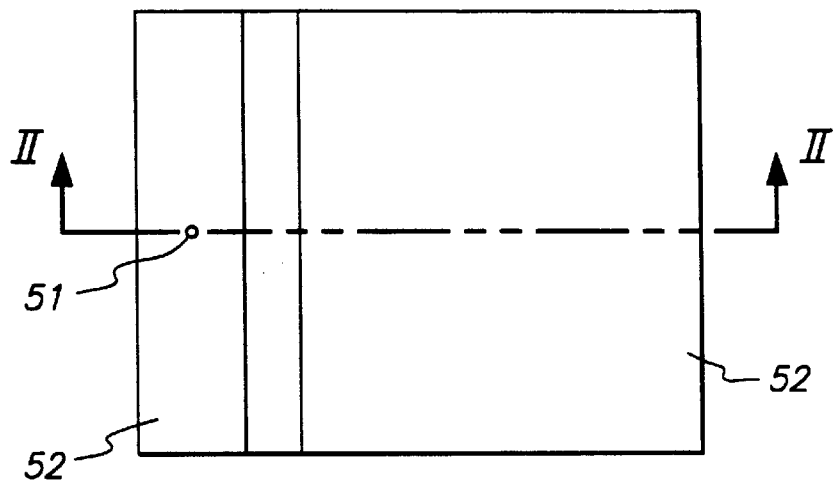
Figure 3:
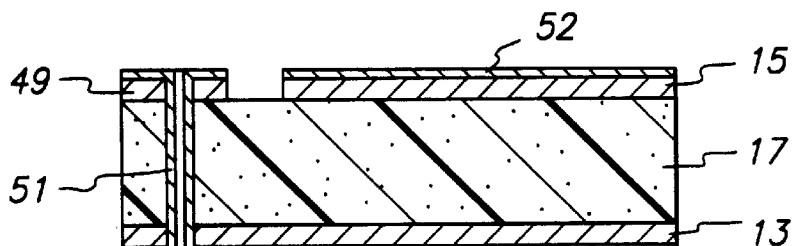

The invention is illustrated in the accompanying drawings, in which the size of the apertures and the thicknesses of the components have been exaggerated in the interests of clarity. FIG. 1 is a perspective view and FIG. 2 is a plan view of a circuit protection device of the invention, and FIG. 3 is a cross section on line II—II of FIG. 2. The device includes a laminar PTC element 17 having a first face to which first laminar electrode 13 is attached and a second face to which second laminar electrode 15 is attached. Also attached to the second face is an additional laminar conductive member 49 which is not electrically connected to electrode 15. Cross-conductor 51 lies within an aperture defined by first electrode 13, PTC element 17 and additional member 49. The cross-conductor is a hollow tube formed by a plating process which also results in a plating 52 on the surfaces of the device which were exposed during the plating process.

Figure 4:
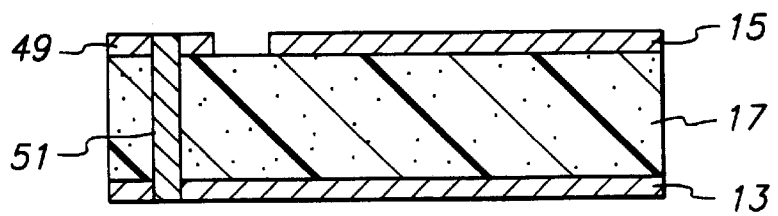

FIGS. 4 and 5 are similar to FIG. 2 but show cross-conductors which are in the form of a metal rod (FIG. 4) or a rivet (FIG. 5)

FIG. 6 is a perspective view and FIG. 7 is a plan view of another circuit protection device of the invention which has been soldered to a circuit board, and FIG. 8 is a cross section on line VI—VI of FIG. 6. The device is similar to that shown in FIGS. 1–3 but has been made symmetrical so that it can be placed on a circuit board either way up. Thus the device includes a second cross-conductor 31 which connects the second electrode 15 to a second additional member 35. The cross-conductors were made by plating the apertures (and the other exposed surfaces) first with copper and then with solder. The device has been soldered to traces 41 and 43 on an insulating substrate 9. During the soldering process the solder plating on the device flows and completely fills the apertures.

Figure 9:
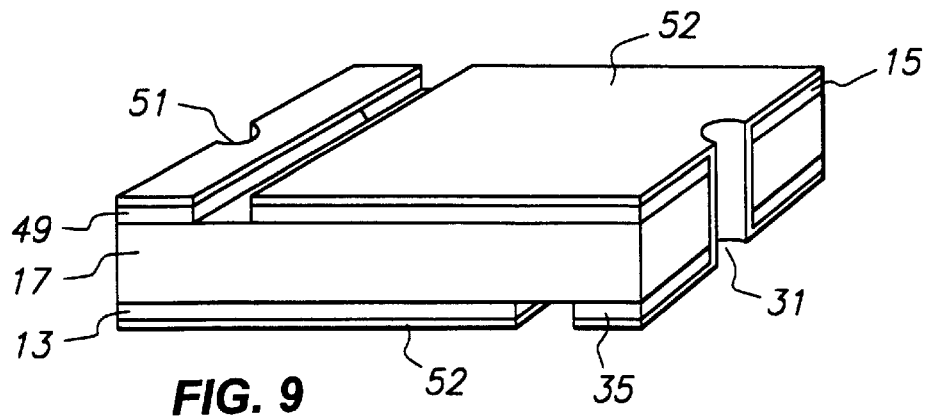
FIG. 9 is a perspective view of a device of the first aspect of the invention.
Figure 10:
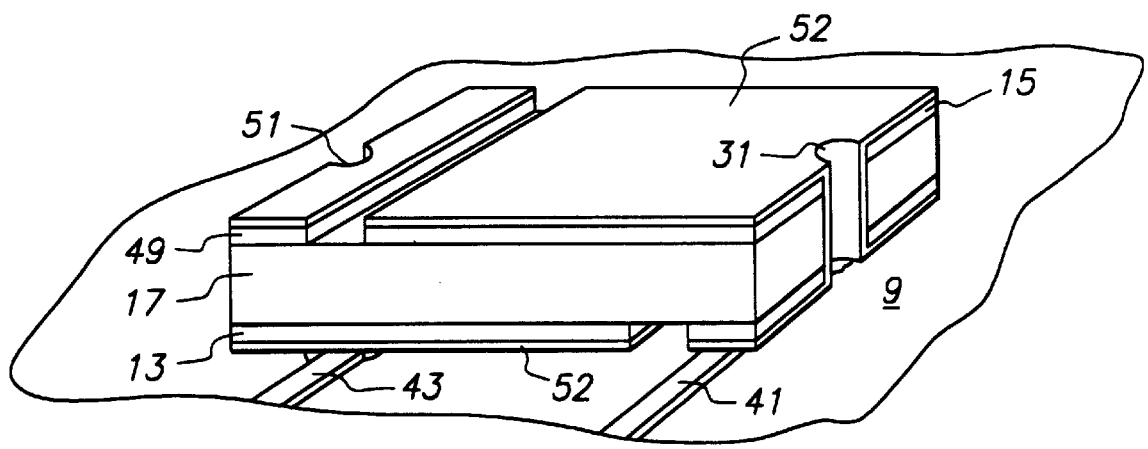
FIG. 10 is a perspective view of the device of FIG. 10 mounted on a printed circuit board.

FIG. 9 is a perspective view of a device which is similar to that shown in FIG. 5–8, but in which each of the apertures has an open cross section which is a half circle. FIG. 10 is a perspective view of the device of FIG. 9 which has been soldered to traces 41 and 43 on an insulating substrate 9.

Figure 11:
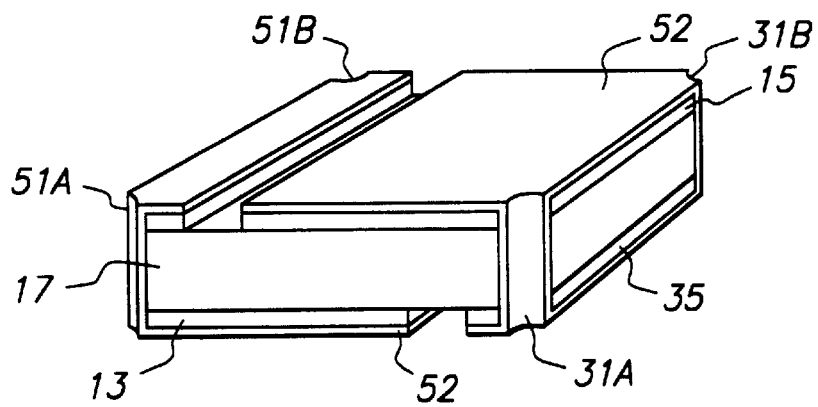
FIG. 11 is a perspective view of a device of the first aspect of the invention.

FIG. 11 is a perspective view of a device which is similar to that shown in FIG. 9 except that each of the apertures having a half-circle cross section has been replaced by two apertures each having a quarter circle cross section and containing cross-conductors 31A, 31B, 51A and 51B.

Figure 12:
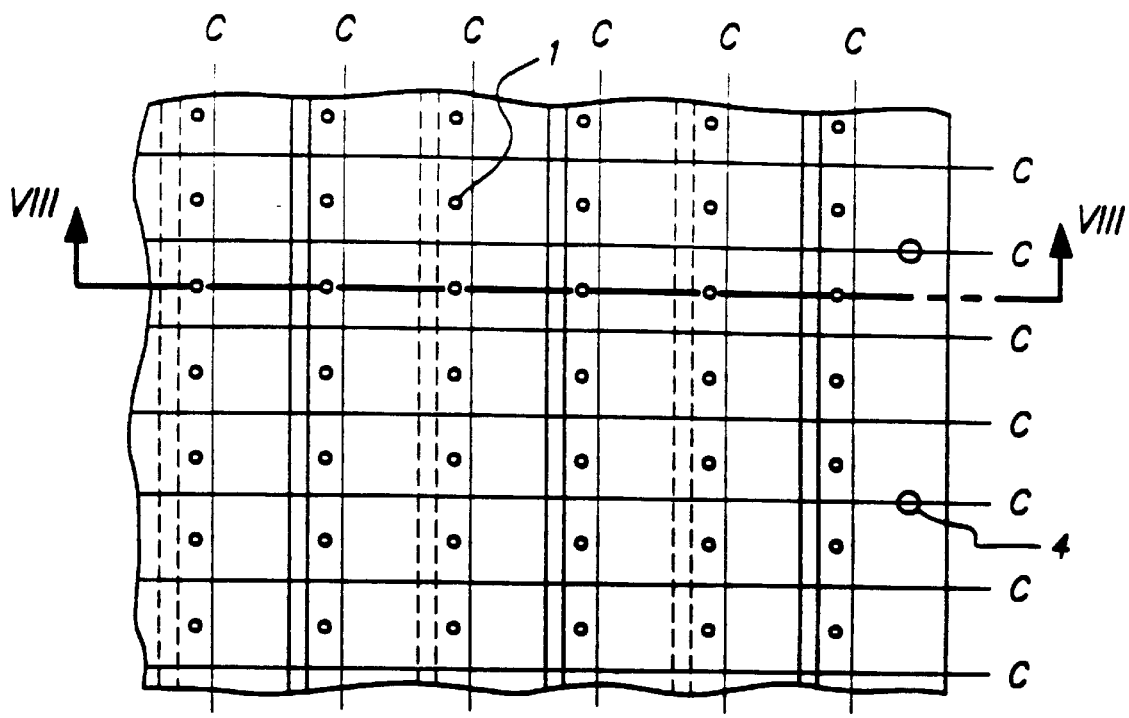
FIGS. 12 and 13 are plan and cross sectional views of part of an assembly of the second aspect of the invention which can be divided into a plurality of individual devices of the first aspect of the invention.
Figure 13:
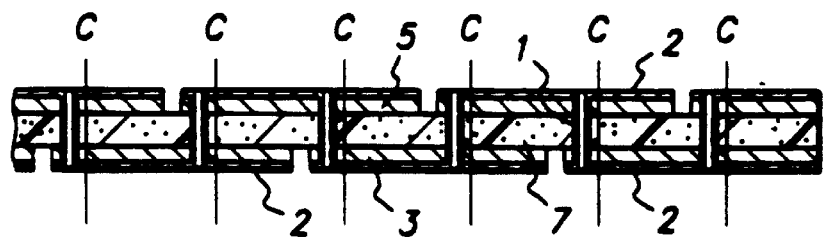

FIG. 12 is a plan view of a part of an assembly of the invention which can be divided into a number of individual devices as shown in FIGS. 1–3, and FIG. 13 is a cross section on line VIII—VIII of FIG. 12. The assembly includes a laminar PTC element 7 having a first face to which first laminar conductive member 3 is attached and a second face to which second laminar conductive member 5 is attached. The conductive members 3 and 5 are not continuous but are in the form of parallel strips formed by removing, e.g. by etching, strips of electrode material from a corresponding continuous member. The material is removed in staggered strips alternately from opposite sides of the assembly, in order to balance the physical stresses in the product. Before the etching step, a plurality of holes, arranged in a regular pattern, have been drilled through the PTC element 7 and the laminar members 3 and 5, and the assembly has then been plated to provide a tubular cross-conductor 1 in each of the apertures (and a plating 2 on other exposed surfaces of the assembly). The assembly can be converted into a plurality of devices by dividing it along the lines marked C. At the edge of the assembly, there are registration holes 4 for use in locating the holes to be drilled through the element 7 and members 3 and 5, and in locating the lines of division C.

Figure 14:
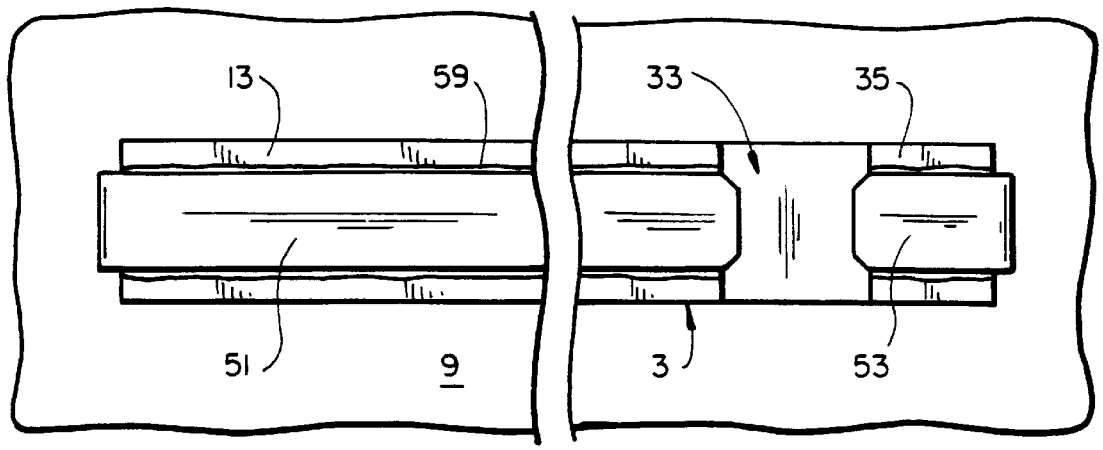
FIG. 14 is a top view of an assembly which includes a device of the fourth aspect of the invention mounted on a circuit board and parallel thereto.
Figure 15:
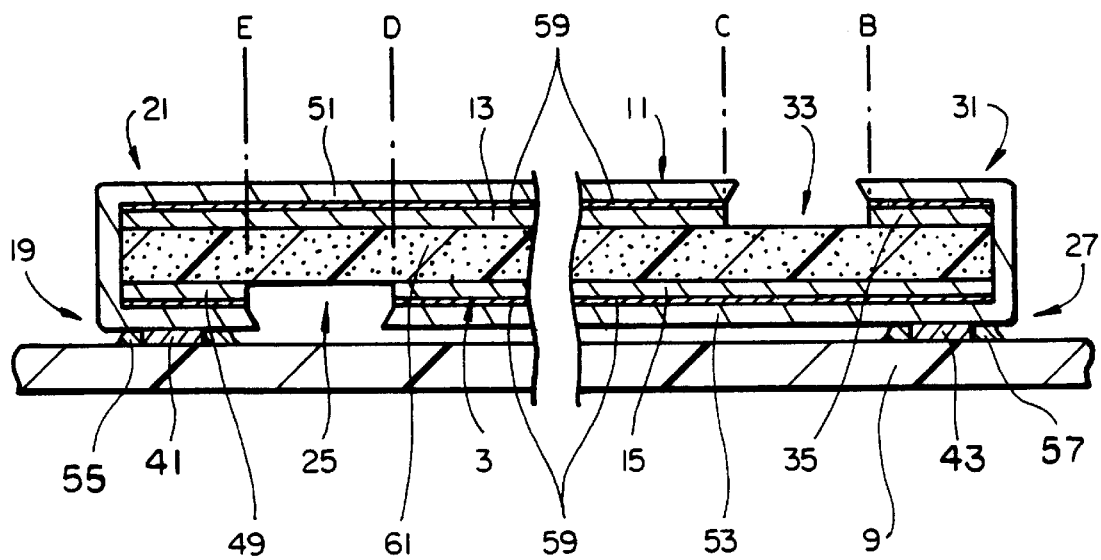
FIG. 15 is a cross-sectional view through the thickness of the assembly of FIG. 14.

FIG. 14 is a top view of another assembly 1 of the invention and FIG. 15 is a cross-sectional view through the thickness of the assembly 1 in which the electrical device 3 is suitable for installing as a surface mounted device. In this assembly, the electrical device 3 comprises a laminar resistive element 61 which is laminated to the main portion of the first electrode 13 and the first residual conductive member 35 and to the main portion of the second electrode 15 and the second residual conductive member 49. (The main portion 11 of the device lies between lines C and D.) Attached to first connection leg 19 around first distal sub-portion 21 is U-shaped first connector 51. Attached to second connection leg 27 around second distal sub-portion 31 is U-shaped second connector 53. A solder joint 59 lies between the periphery of the first connector 51 and the first electrode 13 and between the periphery of the second connector 53 and the second electrode 15. First bridge sub-portion 25 lies between lines D and E and second bridge sub-portion 33 lies between lines B and C. Electrical connection is made from the first connector 51 to a first metal conductor 41 secured to insulating substrate 9 by means of first solder joint 55, and from the second connector 53 to second metal connector 43 secured to the insulating substrate 9 by means of second solder joint 57.

EXAMPLE

A conductive polymer composition was prepared by pre blending 48.6% by weight high density polyethylene (Petrothene™ LB 832, available from USI) with 51.4% by weight carbon black (Raven™ 430, available from Columbian Chemicals), mixing the blend in a Banbury™ mixer, extruding the mixed compound into pellets, and extruding the pellets though a 3.8 cm (1.5 inch) extruder to produce a sheet with a thickness of 0.25 mm (0.010 inch). The extruded sheet was cut into 0.31×0.41 meter (12×16 inches) pieces and each piece was stacked between two sheets of 0.025 mm (0.001 inch) thick electrodeposited nickel foil (available from Fukuda). The layers were laminated under heat and pressure to form a plaque with a thickness of about 0.25 mm (0.010 inch). Each plaque was irradiated to 10 Mrad. Each plaque was used to prepare approximately 7000 devices, each having the configuration shown in FIGS. 1 and 2.

Holes with a diameter of 0.25 mm (0.10 inch) were drilled through the thickness of the plaque in a regular pattern to provide one hole for each device. Each hole was deburred and cleaned. The surface of both the nickel foil layers and the conductive polymer surrounding the drilled hole were sensitized using a palladium/copper solution. A copper layer approximately 0.076 mm (0.003 inch) thick was electroless plated onto the sensitized surfaces and then a 0.025 mm (0.001 inch) thick layer of tin-lead solder was electroless plated onto the copper surface. Using the following standard photoresist process, a pattern was etched onto the plaque. First, a dry film (Mylar™ polyester) resist was laminated onto both surfaces of the plaque and then exposed to ultraviolet light to generate a pattern as shown in FIGS. 7 and 8. Second, a ferric chloride solution was used to chemically etch the pattern. During this step, alternating sections on each side of the plaque were etched away to expose the solder and relieve built-up mechanical stress. Third, the etched plaque was rinsed and the resist was stripped away.

The plaque was sheared and diced to produce individual rectangular electrical devices. Each device had dimensions of 4.57×3.05×0.51 mm (0.180×0.120×0.020 inch). The through-hole was positioned approximately 3.81 mm (0.015 inch) from the shorter edge of the device. A strip of exposed conductive polymer 0.51×3.05 mm (0.020×0.120 inch) was present 0.38 mm (0.015 inch) from the through-hole and 1.02 mm (0.040 inch) from the shorter edge of the device. Each device had a resistance of approximately 300 mohm.

We claim:

1. A circuit protection device which comprises:
   (1) a la first laminar electrode;
   (2) a second laminar electrode;
   (3) a laminar PTC resistive element which (i) exhibits PTC behavior, (ii) comprises a laminar element composed of a PTC conductive polymer, (iii) has a first face to which the first electrode is secured and an opposite second face to which the second electrode is secured, and (iv) defines an aperture which runs between the first and second faces;
   (4) a third laminar conductive member which (i) is secured to the second face of the PTC resistive element in the area of the aperture, and (ii) is spaced apart from the second electrode; and
   (5) a transverse conductive member which
      (a) lies within the aperture defined by the PTC resistive element,
      (b) runs between the first and second faces of the PTC element,
      (c) is secured to the PTC element, and
      (d) is physically and electrically connected to the first laminar electrode and to the third laminar conductive member, but is not connected to the second laminar electrode.

2. A device according to claim 1 wherein the third laminar conductive member is a residual member formed by removing part of a laminar conductive member secured to the second face of the PTC resistive element, thus forming the second electrode and the residual conductive member.

3. A device according to claim 2 which has a resistance of less than 15 ohm and wherein
   (1) the laminar resistive element is composed of a single layer of a PTC conductive polymer which has a resistivity at 25° C. of less than 50 ohm-cm; and
   (2) the first and second electrodes and the residual conductive member are metal foils.

4. A device according to claim 3 which has a resistance of less than 1 ohm and wherein the conductive polymer has a resistivity at 25° C. of less than 5 ohm-cm.

5. A device according to claim 2 wherein the transverse conductive member comprises a plating of a metal on the surface of the PTC resistive element which defines the aperture.

6. A device according to claim 2 wherein the transverse conductive member comprises solder.

7. A device according to claim 2 wherein the aperture has a closed cross section.

8. A device according to claim 2 wherein the aperture has a cross section which is a half circle.

9. A device according to claim 2 wherein the aperture has a cross section which is a quarter circle.

10. A device according to claim 2 which comprises two or more said transverse conductive members.

11. A device according to claim 2 which has a surface area of at most 15 mm$^2$.

12. A circuit protection device which comprises
   (1) a first laminar electrode;
   (2) a second laminar electrode;
   (3) a laminar PTC resistive element which (i) exhibits PTC behavior, (ii) comprises a laminar element composed of a PTC conductive polymer, (iii) has a first face to which the first electrode is secured and an opposite second face to which the second electrode is secured, and (iv) defines first and second apertures which runs between the first and second faces;
   (4) a third laminar conductive member which (i) is secured to the second face of the PTC resistive element in the area of the first aperture, and (ii) is spaced apart from the second electrode;
   (5) a fourth laminar conductive member which (i) is secured to the first face of the PTC resistive element in the area of the second aperture, and (ii) is spaced apart from the first electrode;
   (6) a first transverse conductive member which
      (a) lies within the first aperture defined by the PTC resistive element,
      (b) runs between the first and second faces of the PTC element,
      (c) is secured to the PTC element, and
      (d) is physically and electrically connected to the first laminar electrode and to the third laminar conductive member, but is not connected to the second laminar electrode; and
   (7) a second transverse conductive member which
      (a) lies within the second aperture defined by the PTC resistive element,
      (b) runs between the first and second faces of the PTC element,
      (c) is secured to the PTC element, and
      (d) is physically and electrically connected to the second laminar electrode and to the fourth laminar conductive member, but is not connected to the first laminar electrode.

13. A device according to claim 12 wherein the third laminar conductive member is a residual member formed by removing part of a laminar conductive member secured to the second face of the PTC resistive element, thus forming the second electrode and the third conductive member; and the fourth laminar conductive member is a residual member formed by removing part of a laminar conductive member secured to the first face of the PTC resistive element, thus forming the first electrode and the fourth conductive member.

14. A device according to claim 12 which has a resistance of less than 15 ohm and wherein the laminar resistive element is composed of a single layer of a PTC conductive polymer which has a resistivity at 25° C. of less than 50 ohm-cm.

15. A device according to claim 12 wherein the first and second electrodes and the third and fourth laminar conductive members are metal foils.

16. A device according to claim 12 wherein each of the first and second transverse conductive members comprises a plating of a metal on the surface of the PTC resistive element which defines the aperture.

17. A device according to claim 12 wherein each of the first and second transverse conductive members comprises solder.

18. A device according to claim 12 wherein each of the first and second apertures has an open cross section.

19. A device according to claim 12 wherein each of the first and second apertures has a cross section which is a half circle.

20. A device according to claim 12 wherein each of the first and second apertures has a cross section which is a quarter circle.

21. A device according to claim 12 which has a surface area of at most 20 mm$^2$.

22. A leadless, discrete electrical device exhibiting PTC behavior and adapted for mounting to a generally planar surface of an associated electrical circuit, said device comprising:
   a polymeric PTC element having generally planar opposite faces and opposing ends;
   a first electrode secured to one of the PTC element faces and extending along the length of said PTC element from one end to a first intermediate location;
   a second electrode secured to the other of the PTC element faces and extending along the length of said PTC element from the other end to a second intermediate location;
   a first additional conductive member secured to said one face and extending along the length of said PTC element from the other end to a third intermediate location spaced from said first intermediate location;
   a second additional conductive member secured to said other face and extending along the length of said PTC element from the one end to a fourth intermediate location spaced from said second intermediate location;
   each of said PTC element, said first electrode and said second additional conductive member having an open aperture at said one end, thereby forming a first recess in said device;
   a first cross-conductor plated in said first recess to electrically connect said first electrode and said second additional conductive member;
   each of said second electrode, said PTC element and said first additional conductive member having an open aperture at said other end, thereby forming a second through hole in said device; and
   a second cross-conductor plated in said second recess to electrically connect said second electrode and said first additional conductive member.

23. A device according to claim 22 wherein each of said first and second electrodes extends along more than one-half the length of said PTC element.

24. A device according to claim 22 wherein said device has two outwardly facing sides each comprising one electrode and one additional conductive member, and wherein each side has the same geometric configuration.

25. A device according to claim 22 wherein said device has external dimension such that it occupies a maximum of 15$^2$ on the surface electrical circuit.

26. A leadless, discrete electrical device exhibiting PTC behavior and adapted for mounting to a generally planar surface of an associated electrical circuit, said device comprising:
   a polymeric PTC element having generally planar opposite faces and opposing ends;
   a first electrode secured to one of the PTC element faces and extending along the length of said PTC element from one end to a first intermediate location;
   a second electrode secured to the other of the PTC element faces and extending along the length of said PTC element from the other end to a second intermediate location;

a first additional conductive member secured to said one face and extending along the length of said PTC element from the other end to a third intermediate location spaced from said first intermediate location;

a second additional conductive member secured to said other face and extending along the length of said PTC element from the one end to a fourth intermediate location spaced from said second intermediate location;

each of said PTC element, said first electrode and said second additional conductive member having a closed aperture adjacent said one end, thereby forming a first through hole in said device;

a first cross-conductor plated in said first through hole to electrically connect said first electrode and said second additional conductive member;

each of said second electrode, said PTC element and said first additional conductive member having a closed aperture adjacent said other end, thereby forming a second through hole in said device; and a second cross-conductor plated in said second through hole to electrically connect said second electrode and said first additional conductive member.

27. A device according to claim 26 wherein each of said first and second electrodes extends along more than one-half the length of said PTC element.

28. A device according to claim 26 wherein said device has two outwardly facing sides each comprising one electrode and one additional conductive member, and wherein each side has the same geometric configuration.

29. The electrical device according to claim 26 wherein said device has external dimensions such that it occupies a maximum of 20 mm$^2$ on the surface of said associated electrical circuit.

30. A leadless, discrete electrical device exhibiting PTC behavior and adapted for mounting to a generally planar surface of an associated electrical circuit, said device comprising:

a polymeric PTC element having generally planar opposite faces and opposing ends;

a first foil electrode secured to one of the PTC element faces and extending along more than one-half the length of said PTC element from one end to a first intermediate location;

a second foil electrode secured to the other of the PTC element faces and extending along more than one-half the length of said PTC element from the other end to a second intermediate location;

a first additional conductive foil member secured to said one face and extending along the length of said PTC element from the other end to a third intermediate location spaced form said first intermediate location;

a second additional conductive foil member secured to said other face and extending along the length of said PTC element from the one end to a fourth intermediate location spaced from said second intermediate location;

each of said PTC element, said first electrode and said second additional conductive member having an open aperture at said one end, thereby forming a first recess in said device;

a first cross-conductor plated in said first recess to electrically connect said first electrode and said second additional conductive member;

each of said second electrode, said PTC element and said first additional conductive member having an open aperture at said other end, thereby forming a second recess in said device; and a second cross-conductor plated in said second recess to electrically connect said second electrode and said first additional conductive member.

31. The electrical device of claim 30 wherein said device has two outwardly facing sides each comprising one electrode and one additional conductive member, and wherein each side has the same geometric configuration.

32. The electrical device of claim 30 wherein said device has external dimensions such that it occupies a maximum of 15 mm$^2$ on the surface of said associated electrical circuit.

33. A circuit protection device which comprises (A) a main portion which comprises
  (a) a main part of a first laminar electrode;
  (b) a main part of a second laminar electrode;
  (c) a main part of a laminar resistive element, said laminar resistive element (i) exhibiting PTC behavior, (ii) comprising a laminar element composed of a PTC conductive polymer, and (iii) having a first face to which the first electrode is secured and an opposite second face to which the second electrode is secured;

and (B) a connection leg which extends away from the main portion, and which comprises
  (a) a distal portion which
    (i) is spaced away from the main portion; and
    (ii) comprises a residual laminar conductive member which is secured to the second face of the laminar resistive element and is spaced apart from the second electrode; a distal part of the first electrode; a distal part of the resistive element; and an electrical connector which contacts the distal part of the first electrode and the distal part of the resistive element, and which extends beyond the second face of the resistive element to contact the residual laminar conductive member; and
  (b) a bridge portion which
    (i) lies between the distal portion and the main portion of the device,
    (ii) emends across the width of the connection leg,
    (iii) comprises a bridge pant of the first electrode and a bridge part of the resistive element, and
    (iv) does not include any part of the second electrode;

the main, bridge and distal parts of the first electrode being integral with each other; the main, bridge and distal parts of the resistive element being integral with each other; and the residual conductive member being such that, in the absence of the bridge portion, it would be integral with the second electrode;

whereby the device can be placed flat on a planar insulating substrate having first and second appropriately spaced-apart metal conductors on the surface thereof, with the electrical connector adjacent the first metal conductor, and the second electrode adjacent the second metal conductor; and electrical connection can be made (a) between the first metal conductor and the first electrode, through the electrical connector, and (b) between the second conductor and the second electrode.

34. A device according to claim 33 wherein the contacting surfaces of the electrical connector, the distal part of the first electrode, and the residual conductive member are soldered together.

35. A device according to claim 33 wherein the electrical connector is a U-shaped member which extends around the end of the distal portion.

36. A device according to claim 35 wherein the contacting surfaces of the electrical connector, the distal part of the first electrode and the residual conductive member are coated with solder so that they can be soldered together by exposing them to heat.

37. A device according to claim 33 which has a resistance of less than 15 ohm and wherein
   (1) the laminar resistive element is composed of a single layer of a PTC conductive polymer which has a resistivity at 25° C. of less than 7 ohm-cm; and
   (2) the first and second electrodes and the residual conductive member are metal foils.

38. A device according to claim 37 which has a resistance of less than 3 ohms.

39. A circuit protection device which comprises
   (A) a main portion which comprises
      (a) a main part of a fist laminar electrode;
      (b) a main part of a second laminar electrode;
      (c) a main part of a laminar resistive element, said laminar resistive element (i) exhibiting PTC behavior, (ii) comprising a laminar element composed of a PTC conductive polymer, and (iii) having a first face to which the first electrode is secured and an opposite second face to which the second electrode is secured;
   (B) a first connection leg which extends away from the main portion, and which comprises
      (a) a first distal portion which
         (i) is spaced away from the main portion; and
         (ii) comprises a first residual conductive member which is secured to the second face of the laminar resistive element and is spaced apart from the second electrode; a distal part of the first electrode; a first distal part of the resistive element; and a first electrical connector which contacts the distal part of the first electrode and the first distal part of the resistive element, and which extends beyond the second face of the laminar resistive element into contact with the first residual conductive member; and
      (b) a first bridge portion which
         (i) lies between the first distal portion and the main portion of the device,
         (ii) extends across the width of the first connection leg,
         (iii) comprises a bridge part of the first electrode and a first bridge part of the resistive element, and
         (iv) does not include any part of the second electrode;
      the main, bridge and distal parts of the first electrode being integral with each other; the main, first bridge and first distal parts of the resistive element being integral with each other; and the first residual conductive member being such that, in the absence of the first bridge portion, it would be integral with the second electrode; and
   (C) a second connection leg which extends away from the main portion, and which comprises
      (a) a second distal portion which
         (i) is spaced away from the main portion, and
         (ii) comprises a second residual conductive member; a distal part of the second electrode; a second distal part of the resistive element; and a second electrical connector which contacts the distal part of the second electrode and the second distal part of the resistive element, and which extends beyond the second face of the laminar resistive element into contact with the second residual conductive member; and
      (b) a second bridge portion which
         (i) lies between the second distal portion and the main portion of the device,
         (ii) extends across the width of the second connection leg,
         (iii) comprises a bridge part of the second electrode and a second bridge part of the resistive element, and
         (iv) does not include any part of the first electrode;
      the main, bridge and distal parts of the second electrode being integral with each other; the main, second bridge and second distal parts of the resistive element being integral with each other; and the second residual conductive member being such that in the absence of the second bridge portion it would be integral with the first electrode;
   whereby the device can be placed either way up flat on a planar insulating substrate having first and second appropriately spaced-apart metal conductors on the surface thereof, with the first or the second electrical connector adjacent the first metal conductor, and the second or the first electrode adjacent the second metal conductor; and electrical connection can be made (a) between the first metal conductor and the first electrode, through the first electrical connector, or between the first metal conductor and the second electrode, through the second electrical connector, and (b) between the second conductor and the second electrode, or between the second conductor and the first electrode.

40. A device according to claim 39 wherein the contacting surfaces of the first electrical connector, the distal part of the first electrode, and the first residual conductive member are soldered together; and the contacting surfaces of the second electrical connector, the distal part of the second electrode and the second residual conductive member are soldered together.

41. A device according to claim 39 wherein the first electrical connector is a U-shaped member which extends around the end of the first distal portion; and the second electrical connector is a U-shaped member which extends around the end of the second distal portion.

42. A device according to claim 39 wherein the contacting surfaces of the first electrical connector, the distal part of the first electrode and the first residual conductive member are coated with solder so that they can be soldered together by exposing them to heat; and the contacting surfaces of the second electrical connector, the distal part of the second electrode and the second residual conductive member are coated with solder so that they can be soldered together by exposing them to heat.

43. A device according to claim 39 which has a resistance of less than 15 ohm and wherein
   (1) the laminar resistive element is composed of a single layer of a PTC conductive polymer which has a resistivity at 25° C. of less than 7 ohm-cm; and
   (2) the first and second electrodes and the first and second residual conductive members are metal foils.

44. A device according to claim 43 which has a resistance of less than 3 ohms.

45. An assembly which can be divided into a plurality of circuit protection devices, each of said devices comprising
   (1) a first laminar electrode;
   (2) a second laminar electrode;
   (3) a laminar PTC resistive element which (i) exhibits PTC behavior, (ii) comprises a laminar element composed of a PTC conductive polymer, (iii) has a first face to which the first electrode is secured and an opposite second face to which the second electrode is secured, and (iv) defines an aperture which runs between the first and second faces;
(4) a transverse conductive member which
(a) lies within the aperture defined by the PTC resistive element,
(b) runs between the first and second faces of the PTC element,
(c) is secured to the PTC element, and
(d) is physically and electrically connected to the first laminar electrode but is not connected to the second laminar electrode; and
(5) a third laminar conductive member which(a) is secured to the second face of the PTC resistive element in the area of the aperture,(b) is electrically connected to the transverse conductive member, and (c) is spaced apart from the second electrode;
the assembly comprising
(1) a plurality of first laminar conductive members in the form of parallel strips;
(2) a plurality of second laminar conductive members in the form of strips which are parallel to each other and to the first laminar conductive members, but which are staggered in relation to the first conductive members;
(3) a laminar PTC resistive element which (i) exhibits PTC behavior, (ii) comprises a laminar element composed of a PTC conductive polymer, (iii) has a first face to which the first conductive members are secured and an opposite second face to which the second conductive members are secured, and (iv) defines a plurality of apertures which run between the first and second faces; and
(4) a plurality of transverse conductive members which are arranged in a plurality of straight lines parallel to the first and second laminar conductive members, and each of which
(a) lies within an aperture defined by the PTC resistive element,
(b) runs between the first and second faces of the PTC element,
(c) is secured to the PTC element, and
(d) is physically and electrically connected to one of the first laminar conductive members and to one of the second laminar conductive members.

46. An assembly according to claim 45 wherein
(a) each of the first conductive members contains two adjacent lines of apertures; and
(b) each of the second members contains two adjacent lines of apertures, one of the lines of apertures falling within one first conductive member, and the other of the lines of apertures falling within another first conductive members.

47. An assembly according to claim 45 wherein
(1) the laminar resistive element is composed of a single layer of a PTC conductive polymer which has a resistivity at 25° C. of less than 50 ohm-cm; and
(2) each of the first and second laminar conductive members is a metal foil.

48. An assembly according to claim 46 wherein each of the transverse conductive members comprises a plating of a metal on the surface of the PTC resistive element which defines the aperture within which the transverse conductive member lies.

49. A method of making a plurality of circuit protection devices, each of said devices comprising (1) a first laminar electrode;
(2) a second laminar electrode;
(3) a laminar PTC resistive element which (i) exhibits PTC behavior, (ii) comprises a laminar element composed of a PTC conductive polymer, (iii) has a first face to which the first electrode is secured and an opposite second face to which the second electrode is secured, and (iv) defines an aperture which runs between the first and second faces;
(4) a third laminar conductive member which (i) is secured to the second face of the PTC resistive element in the area of the aperture, and (ii) is spaced apart from the second electrode; and
(5) a transverse conductive member which
(a) lies within the aperture defined by the PTC resistive element,
(b) runs between the first and second faces of the PTC element,
(c) is secured to the PTC element, and
(d) is physically and electrically connected to the first laminar electrode and to the third laminar conductive member, but is not connected to the second laminar electrode; and
the method comprising the steps of
(A) providing an assembly which comprises
(1) a plurality of first laminar conductive members in the form of parallel strips;
(2) a plurality of second laminar conductive members in the form of strips which are parallel to each other and to the first laminar conductive members, but which are staggered in relation to the first conductive members;
(3) a laminar PTC resistive element which (i) exhibits PTC behavior, (ii) comprises a laminar element composed of a PTC conductive polymer, (iii) has a first face to which the first conductive members are secured and an opposite second face to which the second conductive members are secured, and (iv) defines a plurality of apertures which run between the first and second faces; and
(4) a plurality of transverse conductive members, each of which
(a) lies within an aperture defined by the PTC resistive element,
(b) runs between the first and second faces of the PTC element,
(c) is secured to the PTC element, and
(d) is physically and electrically connected to one of the first laminar conductive members and to one of the second laminar conductive members;
(B) dividing the assembly along dividing lines which are parallel to the conductive members and along lines which are at right angles to the conductive members.

50. A method according to claim 49 wherein
(1) the laminar resistive element is composed of a single layer of a PTC conductive polymer which has a resistivity at 25° C. of less than 50 ohm-cm; and
(2) each of the first and second laminar conductive members is metal foil.

51. A method according to claim 49 wherein the transverse conductive member comprises a plating of a metal on the surface of the PTC resistive element which defines the aperture.

52. A method according to claim 49 wherein the dividing lines which are parallel to the first and second conductive members pass through the transverse conductive members.

53. A method according to claim 52 wherein the dividing lines are positioned so that each of the circuit protection devices comprises (1) a first laminar electrode;

(2) a second laminar electrode;

(3) a laminar PTC resistive element which (i) exhibits PTC behavior, (ii) comprises a laminar element composed of a PTC conductive polymer, (iii) has a first face to which the first electrode is secured and an opposite second face to which the second electrode is secured, and (iv) defines first and second apertures which runs between the first and second faces;

(4) a third laminar conductive member which (i) is secured to the second face of the PTC resistive element in the area of the first aperture, and (ii) is spaced apart from the second electrode; and (5) a fourth laminar conductive member which (i) is secured to the first face of the PTC resistive element in the area of the second aperture, and (ii) is spaced apart from the first electrode;

(6) a first transverse conductive member which
   (a) lies within the first aperture defined by the PTC resistive element,
   (b) runs between the first and second faces of the PTC element,
   (c) is secured to the PTC element, and
   (d) is physically and electrically connected to the first laminar electrode and to the first transverse conductive member, but is not connected to the second laminar electrode; and (7) a second transverse conductive member which
   (a) lies within the second aperture defined by the PTC resistive element,
   (b) runs between the first and second faces of the PTC element,
   (c) is secured to the PTC element, and
   (d) is physically and electrically connected to the second laminar electrode and to the second transverse conductive member, but is not connected to the first laminar electrode.

54. An electrical assembly which comprises (A) a printed circuit board including fist and second conductive traces on a surface thereof, and (B) an electrical device according to claim 26, the third laminar conductive member being soldered to the first conductive trace and the second electrode being soldered to the second conductive trace.

55. An electrical assembly which comprises (A) a printed circuit board including first and second conductive traces on a surface thereof, and (B) an electrical device according to claim 58, the electrical connector being soldered to the first conductive trace and the second electrode being soldered to the second conductive trace.

* * * * *

UNITED STATES PATENT AND TRADEMARK OFFICE
CERTIFICATE OF CORRECTION

PATENT NO. : 5,852,397

DATED : December 22, 1998

INVENTOR(S) : Chan et al.

It is certified that error appears in the above-identified patent and that said Letters Patent is hereby corrected as shown below:

Column 8, line 66, replace "(Fahey et al," by --(Fahey et al),--.

Claim 1, line 2, before "first" delete "1a".

Claim 25, line 3, replace "$15^2$ on the surface electrical circuit." by --15 mm$^2$ on the surface of said associated electrical circuit.--.

Claim 30, line 18, replace "form" by --from--.

Claim 33, line 30, replace "emends" by --extends--.

Claim 33, line 31, replace "pant" by --part--.

Claim 39, line 3, replace "fist" by --first--.

Claim 54, line 2, replace "fist" by --first--.

Claim 55, line 4, replace "58" by --33--.

Signed and Sealed this

Eighth Day of June, 1999

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,852,397  Page 2 of 2

DATED : Chan et al.

INVENTOR(S) : December 22, 1998

It is certified that error appears in the above-identified patent and that said Letters Patent is hereby corrected as shown below:

Figure 8 of the Drawing, replace reference numeral "13" on the right hand side of Figure 8, under reference numeral "17", by --35--. The corrected Figure 8 will then be

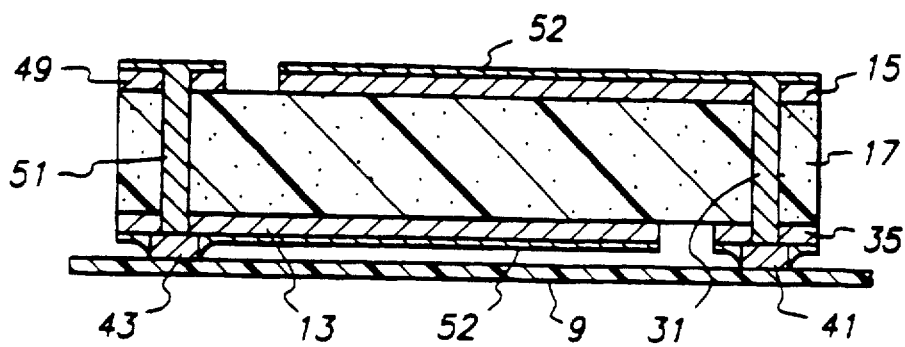

*FIG. 8*